US011642005B2

(12) United States Patent
Kubota et al.

(10) Patent No.: US 11,642,005 B2
(45) Date of Patent: May 9, 2023

(54) ENDOSCOPE SYSTEM, ENDOSCOPE IMAGE PROCESSING METHOD, AND STORAGE MEDIUM

(71) Applicant: OLYMPUS CORPORATION, Tokyo (JP)

(72) Inventors: Akihiro Kubota, Kokubunji (JP); Katsuyoshi Taniguchi, Hino (JP); Yamato Kanda, Hino (JP); Mitsutaka Kimura, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 212 days.

(21) Appl. No.: 17/329,446

(22) Filed: May 25, 2021

(65) Prior Publication Data

US 2021/0274999 A1    Sep. 9, 2021

Related U.S. Application Data

(63) Continuation of application No. PCT/JP2018/043699, filed on Nov. 28, 2018.

(51) Int. Cl.
*G06T 7/62*    (2017.01)
*G06T 7/50*    (2017.01)
(Continued)

(52) U.S. Cl.
CPC ...... *A61B 1/00055* (2013.01); *A61B 1/00045* (2013.01); *A61B 1/000094* (2022.02);
(Continued)

(58) Field of Classification Search
CPC .......... A61B 1/00055; A61B 1/000094; A61B 1/00045; G06T 7/62; G06T 7/50;
(Continued)

(56) References Cited

U.S. PATENT DOCUMENTS 10,282,835 B2 *  5/2019  Reicher ................. G16H 15/00
10,456,072 B2 * 10/2019  Okabe .................... A61B 5/743
(Continued)

FOREIGN PATENT DOCUMENTS

EP            3360461 A1 *  8/2018   ......... A61B 1/00009
JP       2007-244518 A      9/2007
(Continued)

OTHER PUBLICATIONS

International Search Report dated Jan. 29, 2019 issued in PCT/JP2018/043699.

*Primary Examiner* — Shefali D Goradia
(74) *Attorney, Agent, or Firm* — Scully, Scott, Murphy & Presser, P.C.

(57) ABSTRACT

A processor of an endoscope system detects from the observation images a lesion area which is an observation target of the endoscope, judges a level of an oversight risk which is a risk that an operator may overlook the lesion area, on the basis of the observation images, and controls notification methods of detection of the lesion area on the basis of the level of the oversight risk. The processor displays the marker image indicating the lesion area only in a second image region of the display apparatus when a level of the oversight risk relating to the lesion area is a first level and displays the marker image in both a first image region and the second image region which is smaller than the first image region when a level of the oversight risk relating to the lesion area is a second level higher than the first level.

21 Claims, 7 Drawing Sheets

(51) Int. Cl.

| | |
|---|---|
| *A61B 1/00* | (2006.01) |
| *G06T 7/70* | (2017.01) |
| *G06T 7/00* | (2017.01) |
| *G06T 7/20* | (2017.01) |
| *G06T 11/00* | (2006.01) |
| *G08B 5/22* | (2006.01) |
| *H04N 7/18* | (2006.01) |
| *H04N 23/50* | (2023.01) |

(52) U.S. Cl.
CPC ............. *G06T 7/0014* (2013.01); *G06T 7/20* (2013.01); *G06T 7/50* (2017.01); *G06T 7/62* (2017.01); *G06T 7/70* (2017.01); *G06T 11/001* (2013.01); *G08B 5/22* (2013.01); *H04N 7/181* (2013.01); *G06T 2207/10068* (2013.01); *G06T 2207/30096* (2013.01); *H04N 23/555* (2023.01)

(58) Field of Classification Search
CPC ........... G06T 7/70; G06T 7/0014; G06T 7/20; G06T 11/001; G06T 2207/10068; G06T 2207/30096; G08B 5/22; H04N 7/181; H04N 23/555
See application file for complete search history.

(56) References Cited

U.S. PATENT DOCUMENTS

| | | | | |
|---|---|---|---|---|
| 11,033,175 | B2* | 6/2021 | Watanabe | .......... A61B 1/00055 |
| 2013/0111387 | A1 | 5/2013 | Li et al. | |
| 2017/0091582 | A1* | 3/2017 | Takata | .................. A61B 5/055 |
| 2018/0235439 | A1 | 8/2018 | Saito | |
| 2018/0243043 | A1 | 8/2018 | Michihata et al. | |
| 2018/0249900 | A1* | 9/2018 | Imaizumi | .............. G06T 7/0012 |
| 2019/0069757 | A1* | 3/2019 | Iwaki | ......................... G06T 7/70 |
| 2021/0149182 | A1* | 5/2021 | Hayami | ............. G02B 23/2484 |

FOREIGN PATENT DOCUMENTS

| | | | |
|---|---|---|---|
| JP | 2007-319327 | A | 12/2007 |
| JP | 2011-255006 | A | 12/2011 |
| JP | 2012-247879 | A | 12/2012 |
| JP | 2013-074397 | A | 4/2013 |
| JP | 2015-160083 | A | 9/2015 |
| JP | 2017-080246 | A | 5/2017 |
| JP | 2018-033657 | A | 3/2018 |
| JP | 2018-138140 | A | 9/2018 |
| WO | 2012/160796 | A1 | 11/2012 |
| WO | 2017/073242 | A1 | 5/2017 |
| WO | 2018/203383 | A1 | 11/2018 |
| WO | WO-2020152758 | A1 * | 7/2020 ......... A61B 1/00006 |

* cited by examiner

ENDOSCOPE SYSTEM, ENDOSCOPE IMAGE PROCESSING METHOD, AND STORAGE MEDIUM

CROSS REFERENCE TO RELATED APPLICATION

This application is a continuation application of PCT/JP2018/043699 filed on Nov. 28, 2018, the entire contents of which are incorporated herein by this reference.

BACKGROUND OF THE INVENTION

1. Field of the Invention

The present invention relates to an endoscope system, an endoscope image processing method, and a storage medium.

2. Description of the Related Art

Endoscopes have conventionally been widely used in a medical field and an industrial field. For example, in the medical field, a surgeon can find and discriminate a lesion area by viewing an endoscope image of inside of a subject displayed at a display apparatus and can perform treatment on the lesion area using a treatment instrument.

In recent years, CAD (computer aided detection/diagnosis) which indicates positions of candidates for a lesion or displays discrimination information on a moving image of an endoscope to prevent the surgeon from overlooking a lesion area, has been developed. For example, an endoscope system has been proposed which, if a lesion area is found by the CAD, notifies the surgeon that the lesion area exists by highlighting the lesion area on an endoscope image with a marker.

While a diagnosis support function is effective for preventing oversight of a lesion area, there is a possibility that a user may overlook a lesion area depending on a condition of an image. Thus, for example, Japanese Patent Application Laid-Open Publication No. 2015-160083, or the like, has proposed an endoscope system having an oversight prevention function, which judges whether or not a user looks at a lesion area by detecting a line of sight of the user, and in a case where it is judged that the user does not look at the lesion area, issues an alarm.

SUMMARY OF THE INVENTION

An endoscope system according to one aspect of the present invention includes a processor including hardware; and a display apparatus, the processor being configured to sequentially input a plurality of observation images obtained by picking up images of an object with an endoscope, detect from the observation images a lesion area which is an observation target of the endoscope, judge a level of an oversight risk which is a risk that an operator may overlook the lesion area, on the basis of the observation images, and control notification methods of detection of the lesion area on the basis of the level of the oversight risk, the display apparatus including a first image region and a second image region that are for displaying a marker image indicating the lesion area, the second image region being smaller than the first image region, to notify the operator of detection of the lesion area on a basis of control of the notification methods, the processor causing the marker image to be displayed only in the second image region in a case where a level of the oversight risk relating to the lesion area is a first level and causing the marker image to be displayed in both the first image region and the second image region in a case where a level of the oversight risk relating to the lesion area is a second level higher than the first level.

An endoscope image processing method according to one aspect of the present invention includes sequentially inputting a plurality of observation images obtained by picking up images of an object with an endoscope, detecting from the observation images a lesion area which is an observation target of the endoscope, judging a level of an oversight risk which is a risk that an operator may overlook the lesion area, on the basis of the observation images, controlling notification methods of detection of the lesion area on the basis of the level of the oversight risk, notifying the operator of detection of the lesion area on a basis of control of the notification methods using a display apparatus including a first image region and a second image region that are for displaying a marker image indicating the lesion area, the second image region being smaller than the first image region, causing the marker image to be displayed only in the second image region in a case where a level of the oversight risk relating to the lesion area is a first level and causing the marker image to be displayed in both the first image region and the second image region in a case where a level of the oversight risk relating to the lesion area is a second level higher than the first level.

A storage medium according to one aspect of the present invention is a non-transitory computer-readable recording medium storing a program to be executed by a computer, the computer-readable storage medium storing an endoscope image processing program for causing the computer to execute sequentially acquiring a plurality of observation images obtained by picking up images of an object with an endoscope, detecting from the observation images a lesion area which is an observation target of the endoscope, judging a level of an oversight risk which is a risk that an operator may overlook the lesion area, on the basis of the observation images, controlling notification methods of detection of the lesion area on the basis of the level of the oversight risk, notifying the operator of detection of the lesion area on a basis of control of the notification methods using a display apparatus including a first image region and a second image region that are for displaying a marker image indicating the lesion area, the second image region being smaller than the first image region, displaying the marker image only in the second image region in a case where a level of the oversight risk relating to the lesion area is a first level and displaying the marker image in both the first image region and the second image region in a case where a level of the oversight risk relating to the lesion area is a second level higher than the first level.

DETAILED DESCRIPTION OF THE PREFERRED EMBODIMENTS

Embodiments of the present invention will be described below with reference to the drawings.

First Embodiment

Figure 1:
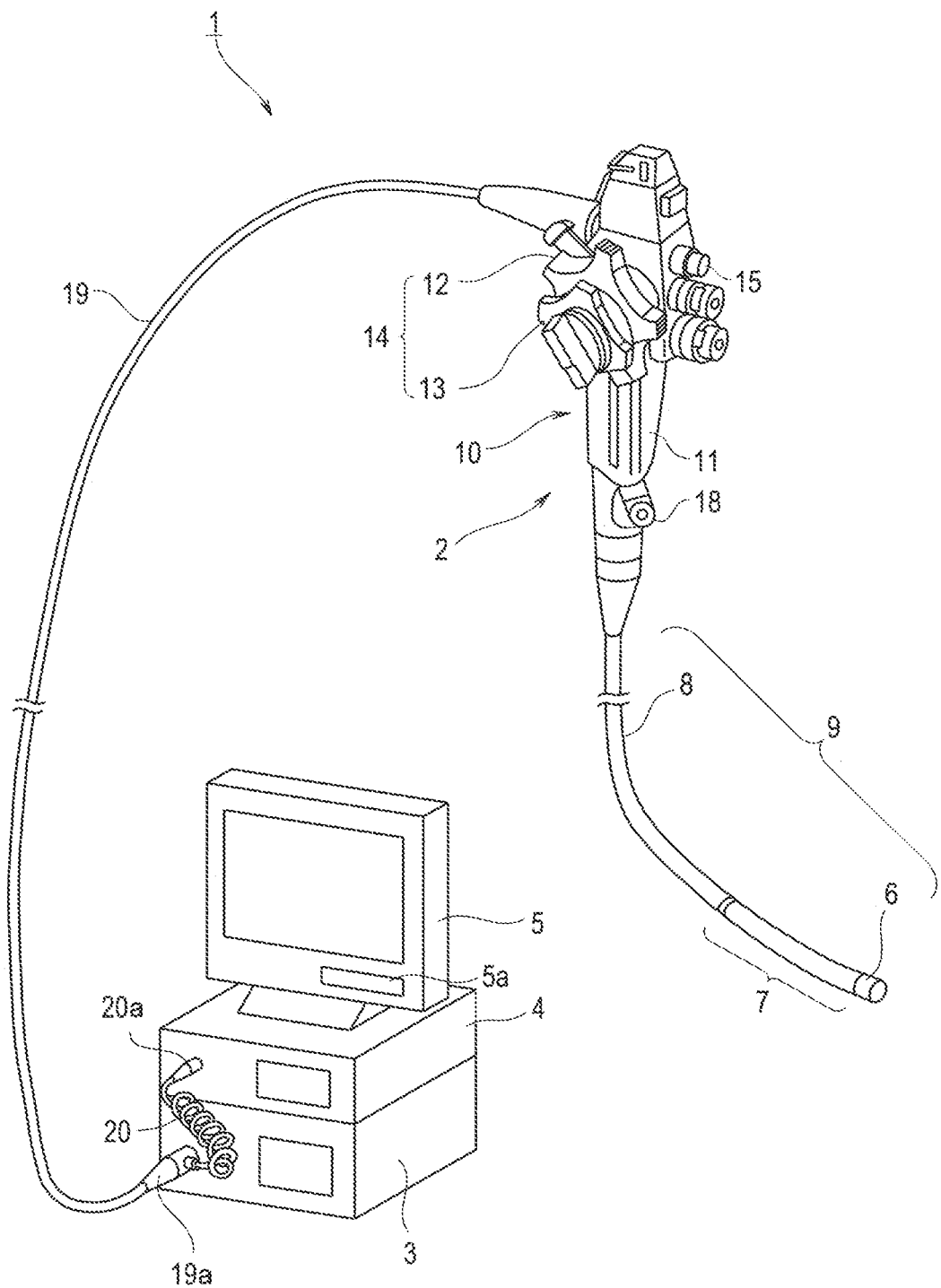
FIG. 1 is a perspective view illustrating an example of an entire configuration of an endoscope system according to embodiments of the present invention.

FIG. 1 is a perspective view illustrating an example of an entire configuration of an endoscope system according to the embodiments of the present invention. An endoscope system 1 of the present embodiment mainly includes an electronic endoscope (hereinafter, simply referred to as an "endoscope") 2 as an endoscope scope, a light source apparatus 3, a processor 4, and a monitor 5.

The endoscope 2 includes a long elongated insertion portion 9, an operation portion 10, and a universal cable 19 which is an electric cable. The insertion portion 9 of the endoscope 2 includes a distal end portion 6, a bending portion 7, and a flexible tube portion 8 in order from a distal end. An illumination window and an observation window which are not illustrated are provided at the distal end portion 6, illumination light is emitted from the illumination window to a subject, and return light from the subject is incident on the observation window. A solid-state image pickup device such as a CCD and a CMOS is disposed at the distal end portion 6 as means for picking up an image of the object, performs photoelectric conversion on an object image by incident light from the observation window and outputs an image pickup signal. The image pickup signal is supplied to the processor 4 via the universal cable 19.

At the operation portion 10, a bending operation portion 14 for bending the bending portion 7 of the insertion portion 9 is rotatably disposed, and switches, and the like, having various kinds of endoscope functions including a focus switch 15 are provided. Note that in the bending operation portion 14, a UD bending operation knob 12 for bending the bending portion 7 in a vertical direction and an RL bending operation knob 13 for bending the bending portion 7 in a horizontal direction are disposed in a superimposed manner.

Further, a connecting portion of the insertion portion 9 and the operation portion 10 includes a grasping portion 11 which also serves as a portion to be grasped by the user, and a treatment instrument channel insertion portion 18 which is disposed at a bend preventing portion provided between the grasping portion 11 and one end of the flexible tube portion 8 of the insertion portion 9 and which is an opening portion of a treatment instrument channel which allows insertion of various kinds of treatment portions disposed at the insertion portion 9.

The universal cable 19 extending from the operation portion 10 includes a scope connector 19a at an extended end, which is detachable from the light source apparatus 3. Further, a coiled coil cable 20 extends from the scope connector 19a, and a scope connector 20a which is a connector detachable from the processor 4 is provided at an extended end of the coil cable 20. Note that the endoscope 2 of the present embodiment transmits illumination light from the light source apparatus 3 to the distal end portion 6 with a light guide cable which is disposed in the universal cable 19, the operation portion 10 and the insertion portion 9 and which is illumination means.

The processor 4, which is electrically connected to the monitor 5 which displays an endoscope image, processes an image pickup signal which is subjected to photoelectric conversion by image pickup means such as a CCD mounted on the endoscope 2, and outputs the processed image pickup signal to the monitor 5 as an image signal.

The monitor 5 is a display apparatus at which the endoscope image is to be displayed. Further, the monitor 5 includes a speaker 5a which outputs voice. Note that the monitor 5 also has a function as a notification unit.

Figure 2:
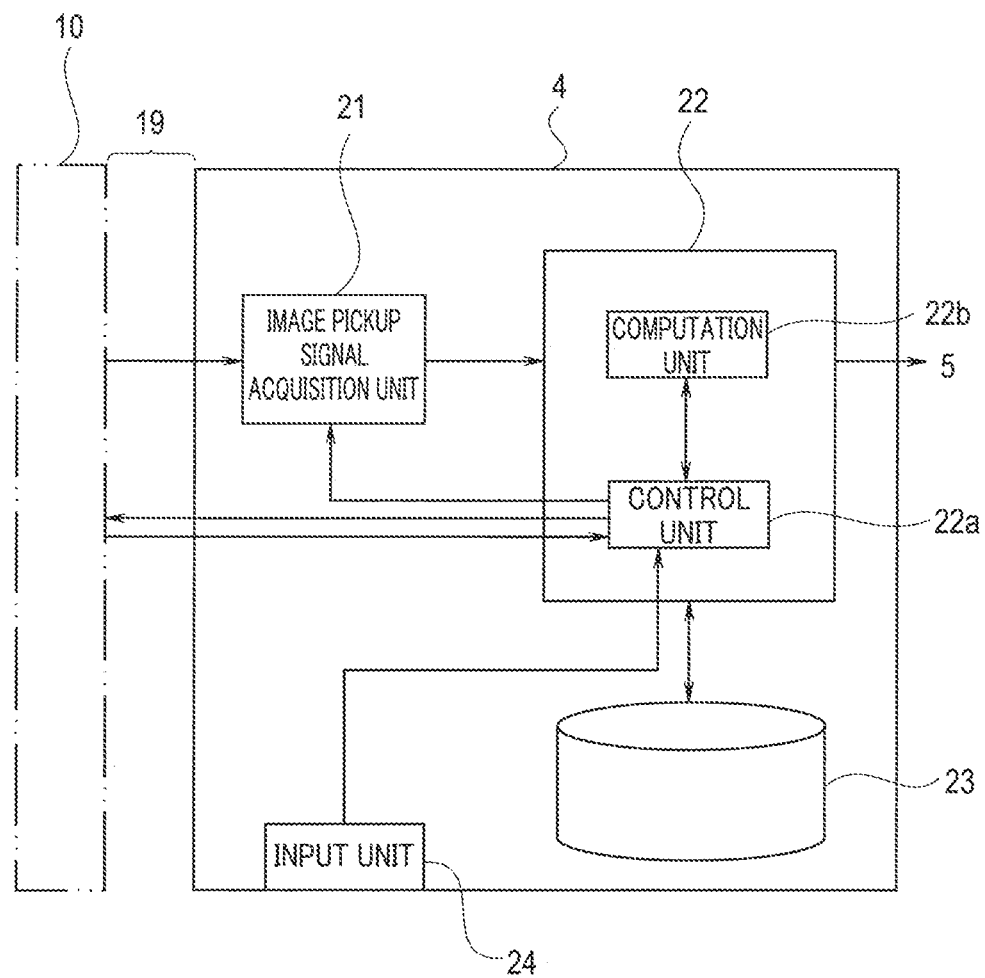
FIG. 2 is a block diagram for explaining an example of a configuration relating to image processing of a processor 4.

FIG. 2 is a block diagram illustrating a configuration relating to image processing of the processor 4. The processor 4 is an image processing apparatus including an image pickup signal acquisition unit 21, a control computation unit 22, a storage apparatus 23, and an input unit 24. The control computation unit 22 is a circuit including a control unit 22a and a computation unit 22b.

The image pickup signal acquisition unit 21 is a circuit which receives and acquires an image pickup signal from an image pickup device of the endoscope 2 under control by the control unit 22a and outputs the image pickup signal to the control computation unit 22.

The control unit 22a, which includes a central processing unit (hereinafter, referred to as a "CPU"), a ROM, a RAM, or the like, controls entire operation of the processor 4, and performs control of driving of the image pickup device of the endoscope 2, control of various kinds of circuits based on various kinds of operation signals from the operation portion 10 of the endoscope 2, control of recording of various kinds of data in the storage apparatus 23 and readout of various kinds of data from the storage apparatus 23 and control of image processing in accordance with an instruction to the input unit 24 by a surgeon.

In other words, the control unit 22a controls operation of the endoscope system 1 on the basis of an instruction or input received at the input unit 24 and outputs a control signal or a setting signal to each unit.

The computation unit 22b is a circuit which executes various kinds of image processing and various kinds of computation processing on the basis of the image pickup signal acquired at the image pickup signal acquisition unit 21 under control by the control unit 22a, generates an image signal of an endoscope image and various kinds of display information to be displayed on the monitor 5 and outputs the image signal and various kinds of display information to the monitor 5.

Note that all or part of the processing of the control unit 22a and the computation unit 22b at the control computation unit 22 may be implemented with a software program.

The storage apparatus 23, which is a large-capacity storage apparatus such as a hard disk apparatus, stores image data of an endoscope image of inside of a subject obtained through endoscopic examination, and various kinds of data such as support information.

The input unit 24, which is an operation panel having various kinds of buttons, is an input apparatus to be used by the surgeon to provide various kinds of settings of the endoscope system 1, various kinds of instructions, or the like, to the processor 4.

Figure 3:
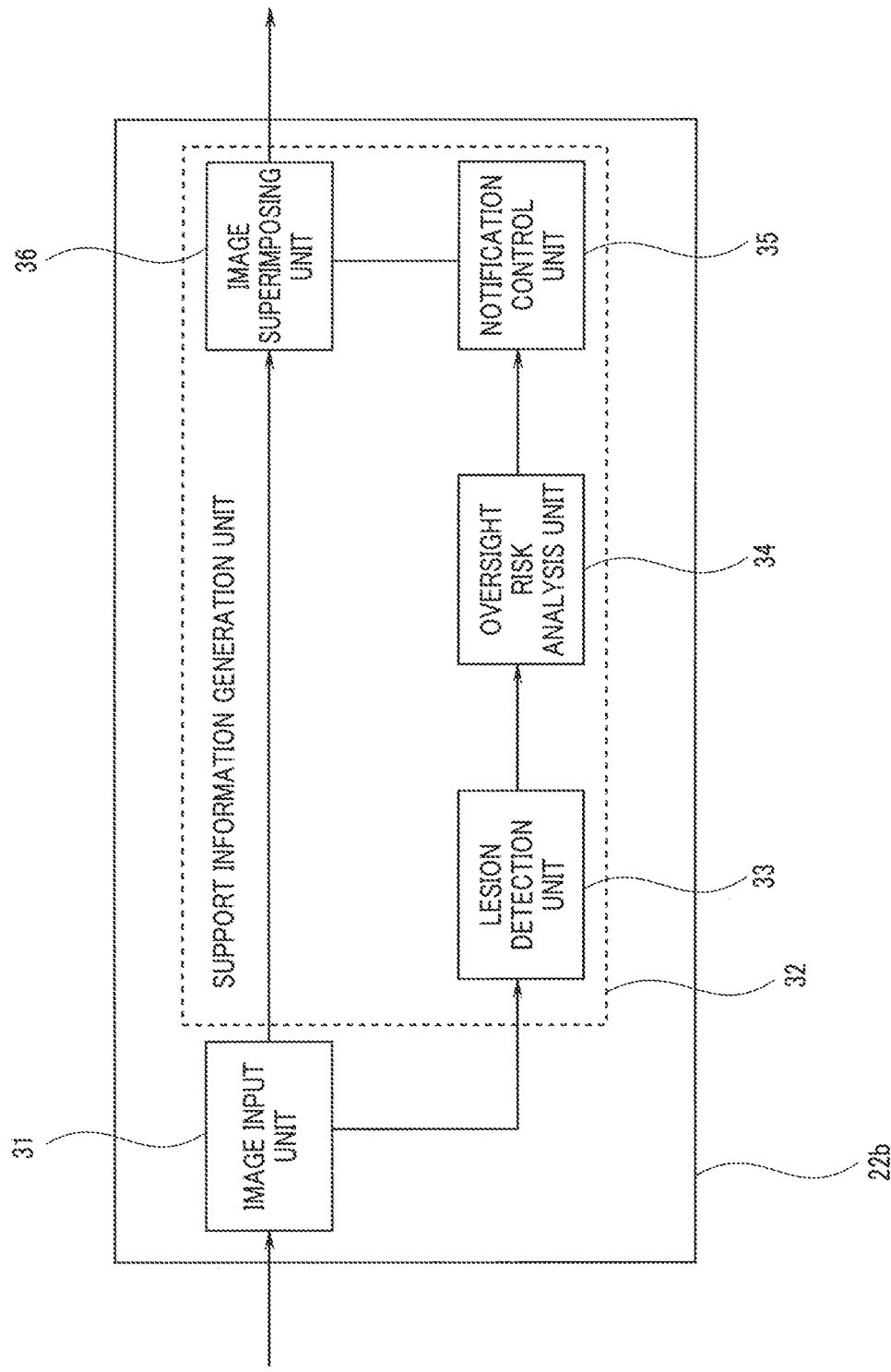
FIG. 3 is a block diagram illustrating a configuration of a computation unit 22b of a control computation unit 22.

FIG. 3 is a block diagram illustrating a configuration of the computation unit 22b of the control computation unit 22 in the present embodiment. The computation unit 22*b* is a circuit including an image input unit 31 and a support information generation unit 32. Note that while not illustrated, the computation unit 22*b* also includes an image generation unit which generates an observation image G1 of an object by performing predetermined processing on the received image pickup signal and sequentially outputs frames of the generated observation image G1 to the image input unit 31 one by one.

The image input unit 31 sequentially outputs the input frames of the observation image G1 to the support information generation unit 32 one by one.

The support information generation unit 32 includes a lesion detection unit 33, an oversight risk analysis unit 34, a notification control unit 35, and an image superimposing unit 26.

The lesion detection unit 33 detects a lesion area included in the frames of the generated image sequentially output from the image input unit 31. The lesion detection unit 33 detects a lesion area from the generated image, for example, by performing processing of applying an image discriminator which has acquired a function of being capable of discriminating a polyp image in advance through a learning method such as deep learning, to the generated image. Note that the lesion area may be detected using other methods as well as the above-described learning method. For example, a polyp candidate detection processing as disclosed in Japanese Patent Application Laid-Open Publication No. 2007-244518, or the like, may be used.

Figure 4:
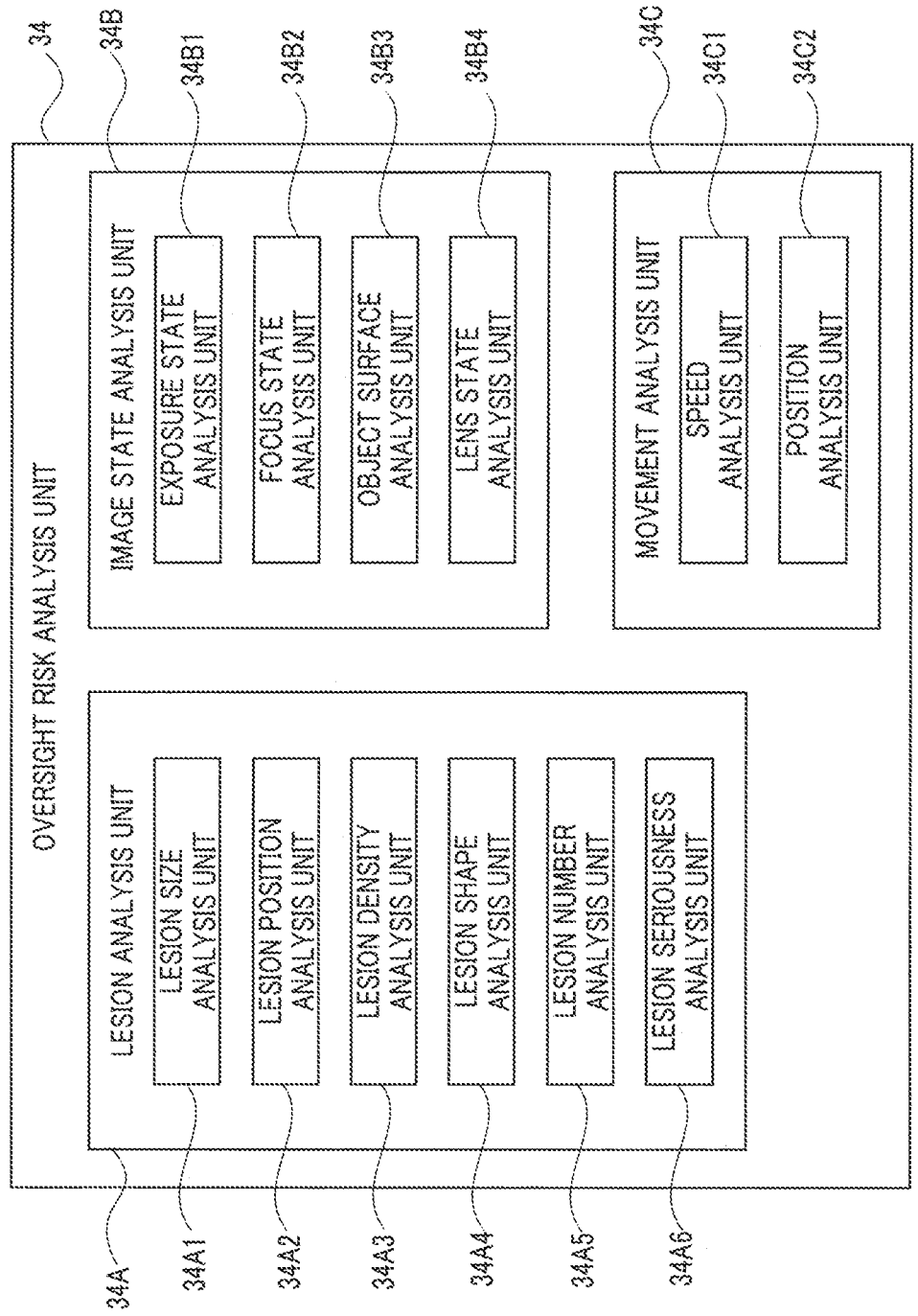
FIG. 4 is a block diagram illustrating a configuration of an oversight risk analysis unit 34.

The oversight risk analysis unit 34 is a circuit which analyzes an image including the lesion area detected by the lesion detection unit 33 and judges a possibility that the surgeon who is the user may overlook the lesion area, as a risk. FIG. 4 is a block diagram illustrating a configuration of the oversight risk analysis unit 34. The oversight risk analysis unit 34 includes a lesion analysis unit 34A, an image state analysis unit 34B, and a movement analysis unit 34C.

The lesion analysis unit 34A analyzes the input image, and determines a size, a position, density, a shape, or the like, of the lesion area to evaluate a risk that the lesion area may be overlooked. The image state analysis unit 34B analyzes the input image, determines whether or not an image pickup state of the image is a state which is appropriate for a diagnosis support function, and evaluates a risk that the lesion area may be overlooked. The movement analysis unit 34C analyzes the input image, determines a degree of movement of the lesion area by the user operating the endoscope 2, and evaluates a risk that the lesion area may be overlooked.

Operation of respective units of the lesion analysis unit 34A, the image state analysis unit 34B and the movement analysis unit 34C illustrated in FIG. 4 will be described later in the corresponding description. FIG. 4 also illustrates components relating to second and third embodiments which will be described after the present embodiment as well as components relating to the present embodiment which will be described below.

The notification control unit 35 controls notification means and a notification method for allowing the user to recognize existence of the lesion area detected at the lesion detection unit 33. In the present embodiment, a notification is made using a display image on the monitor 5. Further, as support information for allowing the surgeon to recognize existence of the lesion area, for example, a marker image which encloses the lesion area is generated and added to the generated image.

The marker image may take any form as long as the marker image can present existence of the lesion area as visual information and may be any image such as a rectangle, a triangle, a circle and a star shape. Further, the marker image may be an image which does not enclose the lesion area if the marker image can indicate existence of the lesion area. For example, existence of the lesion area may be indicated by making brightness or color tone of the lesion area different from peripheral regions. Further, a message indicating the lesion area may be generated as the support information, and the existence of the lesion area may be indicated by displaying the message in a form such as a pop-up message near the lesion area.

The notification control unit 35 controls the notification method of the support information in accordance with the risk that the lesion area may be overlooked evaluated at the oversight risk analysis unit 34. For example, the notification control unit 35 changes color, a thickness and a size of the marker image to be added to the lesion area in accordance with a level of the oversight risk.

Figure 5:
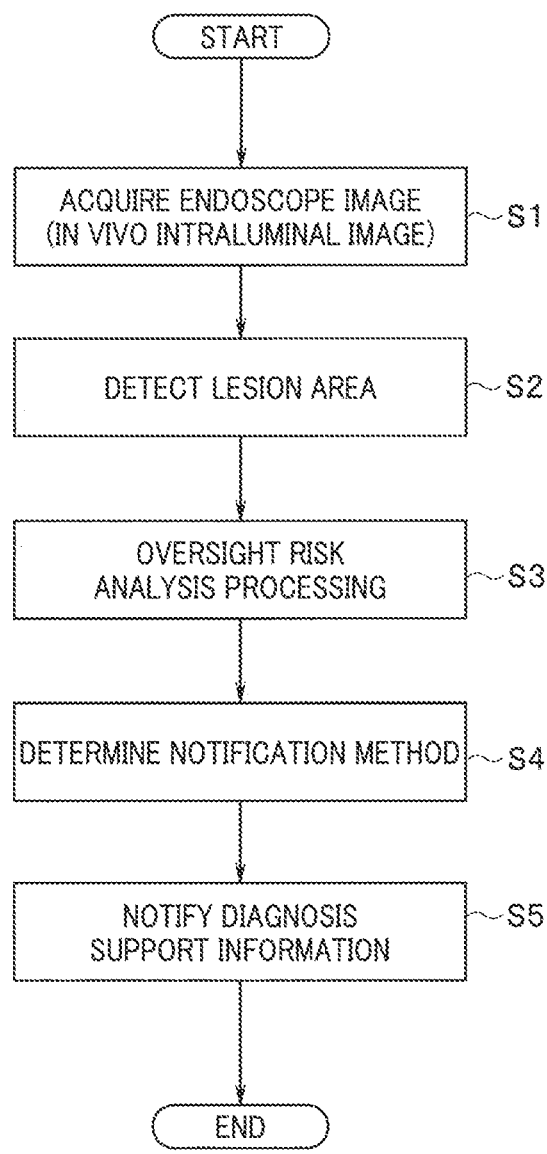
FIG. 5 is a flowchart explaining an example of an endoscope image processing method according to the embodiments of the present invention.

Subsequently, operation of the present embodiment will be described. FIG. 5 is a flowchart explaining an example of an endoscope image processing method according to the embodiments of the present invention, that is, procedure of executing a diagnosis support function to be performed in the endoscope system of the present embodiment.

The computation unit 22*b* acquires an image pickup signal from the endoscope 2 by the control unit 22*a* controlling driving of the light source apparatus 3 and driving of the image pickup device of the endoscope 2 and controlling the image pickup signal acquisition unit 21 in accordance with a set observation mode. The image input unit 31 of the computation unit 22*b* acquires an observation image G1 of an object by performing predetermined processing on the image pickup signal generated at an image generation unit which is not illustrated, and sequentially outputs frames of the observation image G1 to the support information generation unit 32 one by one. In other words, the support information generation unit 32 acquires from the image input unit 31 an endoscope image (observation image G1) which is an in vivo intraluminal image (S1).

The lesion detection unit 33 in the support information generation unit 32 first detects a lesion area Ln from the observation image G1 by performing processing of applying an image discriminator which has acquired a function of being capable of discriminating a polyp image in advance through a learning method such as deep learning, to the observation image G1 (S2). The detection result of the lesion area Ln is output to the oversight risk analysis unit 34.

The oversight risk analysis unit 34 judges a possibility that the lesion area Ln in the observation image G1 may be overlooked, as a risk (oversight risk analysis processing, S3). The oversight risk analysis unit 34 determines a state of the lesion area, a state of the image and an operation state of the endoscope (a movement state of the lesion area in the image) through image analysis and judges an oversight risk.

In a case where an oversight risk is judged from the state of the lesion area, the lesion analysis unit 34A of the oversight risk analysis unit 34 performs analysis processing for judging a risk. Analysis items for judging an oversight risk from the state of the lesion area include, for example, (a) a size of the lesion area Ln, (b) a position of the lesion area Ln in the observation image G1, (c) density of the lesion area Ln, and (d) a shape of the lesion area Ln. The lesion analysis unit 34A performs analysis concerning items selected from these items and judges a risk that the lesion area Ln may be overlooked.

(a) Size of Lesion Area Ln

In a case where the present item is selected as the analysis item, processing described below is performed. A lesion size analysis unit 34A1 in FIG. 4 is involved with the following processing.

The lesion size analysis unit 34A1 first estimates an image pickup distance to each pixel within the image. Here, image pickup distance estimation assuming that an image pickup target is a uniform diffuser based on the image among various publicly-known technologies will be described as estimation of the image pickup distance.

More specifically, first, a low absorption wavelength (for example, a wavelength of red (R)) component for which a degree of absorption or diffusion within an organism is the lowest is selected as a low absorption wavelength component. The low absorption wavelength component is selected to prevent degradation of pixel values by vessels, or the like, on a mucous surface and to obtain pixel value information which correlates most closely with the image pickup distance to the mucous surface. In an image including three components of red (R), green (G) and blue (B), the component of red (R) is selected because the component of red (R) is a component of a wavelength which moves away from an absorption band of blood and which is a long wavelength, and thus, is less likely to be affected by absorption and diffusion within an organism.

Further, the lesion size analysis unit 34A1 estimates an image pickup distance assuming the uniform diffuser based on the pixel value of the low absorption wavelength component. More specifically, the image pickup distance is calculated using the following equation (1).

$$\Gamma = \sqrt{\frac{I \times K \times \cos\theta}{L}} \qquad \text{equation (1)}$$

Here, r indicates an image pickup distance, I indicates radiation intensity of a light source obtained in advance through measurement, and K indicates a diffuse reflection coefficient of the mucous surface which is measured in advance and which is an average value. θ indicates an angle formed by a normal vector of the mucous surface and a vector from the surface to the light source, which is a value determined by positional relationship between the light source at the distal end portion of the insertion portion of the endoscope 2 and the mucous surface, and an average value is set in advance. L indicates an R component value of a pixel of the mucous surface to which the image pickup distance is to be estimated.

Note that variation of pixel values by an optical system or an illumination system which can be a degradation factor for accuracy of each processing may be corrected, or non-mucosal area such as specular reflection, residues and froth may be removed before estimation of the image pickup distance.

While the method based on the image has been described here, the image pickup distance may be calculated on the basis of a ranging sensor, or the like, as other methods.

As described above, after a distance between the endoscope 2 and the lesion area Ln is estimated, the lesion size analysis unit 34A1 provides a threshold smaller than the image pickup distance and a threshold greater than the image pickup distance for the image pickup distance of pixels around the lesion and extracts a region in an image pickup distance band in which the lesion is located through threshold processing. The lesion size analysis unit 34A1 calculates a degree of circularity of the region and, in a case where the degree of circularity is greater than a predetermined value, detects the region as a lumen.

Finally, the lesion size analysis unit 34A1 compares the lumen with the lesion area and estimates the size of the lesion area.

More specifically, the lesion size analysis unit 34A1 estimates an actual size of the lesion by calculating a ratio of a length of the lesion with respect to a circumferential length of the detected lumen. Note that it is also possible to improve accuracy of size estimation by setting a circumferential length of the lumen of each organ site (position) in advance on the basis of anatomy. For example, in a case of colorectal examination, it is possible to improve accuracy of size estimation by estimating a site (position) of a lesion area at large intestine from an insertion amount of the insertion portion and comparing the length with the circumferential length of the lumen set in advance.

As described above, the lesion size analysis unit 34A1 estimates the size of the lesion area Ln by comparing the size with a circular size of the lumen in the endoscope image. In a case where the estimated size of the lesion area Ln is greater than a predetermined size (for example, 5 mm) set in advance, it is determined that the oversight risk is low. On the other hand, in a case where the estimated size of the lesion area Ln is smaller than the predetermined size, it is determined that the oversight risk is high.

(b) Position of Lesion Area Ln in Observation Image G1

In a case where the present item is selected as the analysis item, processing described below is performed. A lesion position analysis unit 34A2 in FIG. 4 is involved with the following processing.

The lesion position analysis unit 34A2 first detects the lesion area Ln from the observation image G1 by performing processing of applying an image discriminator which has acquired a function of being capable of discriminating a polyp image in advance through a learning method such as deep learning to the observation image G1 and acquires position information. Note that the lesion area Ln may be detected using other methods as well as the learning method described above. For example, polyp candidate detection processing, or the like, as disclosed in Japan Patent Application Laid-Open Publication No. 2007-244518 may be used. Further, the position information of the lesion area Ln may be acquired from the lesion detection unit 33.

Next, the position of the lesion area Ln in the observation image G1 is analyzed. An example of a specific method will be described below. First, the observation image G1 is equally divided into three portions in a vertical direction and equally divided into three portions in a horizontal direction to divide the observation image G1 into nine blocks. For example, in a case where the observation image G1 includes 1920×1080 pixels, the observation image G1 is divided into a region (1A) of (0, 0) to (640, 360), a region (1B) of (641, 0) to (1280, 360), a region (1C) of (1281, 0) to (1920, 360), a region (2A) of (0, 361) to (640, 720), a region (2B) of (641, 361) to (1280, 720), a region (2C) of (1281, 361) to (1920, 720), a region (3A) of (0, 721) to (640, 1080), a region (3B) of (641, 721) to (1280, 1080), and a region (3C) of (1281, 721) to (1920, 1080) assuming that an upper left point in the image is an original point (0, 0). Note that an oversight risk (either a high oversight risk or a low oversight risk) is registered in each block.

A block in which the lesion area Ln exists is specified from these nine blocks 1A to 3C and output as the position of the lesion area Ln. Note that in a case where the lesion area Ln exists across a plurality of blocks, a block which has the largest area in which the lesion area Ln exists is specified as a block in which the lesion area Ln exists. Note that a method for specifying the block in which the lesion area Ln exists is not limited to the above-described method, but other methods such as a method in which a pixel located at the center of the lesion area Ln exists is specified as the block in which the lesion area Ln exists. Further, the number of blocks generated by dividing the observation image G1 is not limited to nine blocks, but may be, for example, 2×2=4 blocks, or 4×4=16 blocks.

As described above, the lesion position analysis unit 34A2 estimates the position of the lesion area Ln and determines the oversight risk registered in the block in which the lesion area Ln is located as the oversight risk of the lesion area Ln. In other words, in a case where it is estimated that the lesion area Ln exists in a block for which a high oversight risk is registered, it is determined that the oversight risk of the lesion area Ln is high. On the other hand, in a case where it is estimated that the lesion area Ln exists in a block for which a low oversight risk is registered, it is determined that the oversight risk of the lesion area Ln is low.

Note that the position of the lesion area Ln may be calculated as a distance from a central pixel position of the observation image G1 instead of being calculated as the above-described block position. In this case, in a case where the calculated distance is greater than a threshold set in advance, it is determined that the oversight risk is high. On the other hand, in a case where the calculated distance is smaller than the threshold set in advance, it is determined that the oversight risk is low.

(c) Density of Lesion Area Ln

In a case where the present item is selected as the analysis item, processing described below is performed. A lesion density analysis unit 34A3 in FIG. 4 is involved with the following processing.

The lesion density analysis unit 34A3 extracts density values (luminance values) of respective pixels included in the lesion area Ln, obtains an average value of the density values and sets the average value as a density value of the lesion area Ln. Note that other statistics such as a mode value may be used in calculation of the density value, instead of using the average. In a case where the calculated density value is greater than a threshold (for example, a density value of normal mucosa), it is determined that the oversight risk is low. On the other hand, in a case where the estimated density value of the lesion area Ln is smaller than the threshold, it is determined that the oversight risk is high. Note that a value registered in advance or a value of a normal mucosa portion in the observation image G1 in which the lesion area Ln exists may be used as the density value which becomes a criterion for determination.

(d) Shape of Lesion Area Ln

In a case where the present item is selected as the analysis item, processing described below is performed. A lesion shape analysis unit 34A4 in FIG. 4 is involved with the following processing.

The lesion shape analysis unit 34A4 performs discrimination and classification on the basis of a shape of the lesion area. More specifically, the lesion shape analysis unit 34A4 creates a mask image indicating the lesion area and calculates a shape feature value on the basis of the image. The shape feature value is classified into one of a plurality of classes generated through machine learning using a classifier such as SVM. Here, publicly-known parameters such as a degree of circularity, moment and a fractal dimension are used as the shape feature value.

For example, in a case of a polyp of large intestine, the polyp includes a protruding type (type I) and a surface type (type II), and the shape of the lesion area Ln is classified into one of the protruding type and the surface type. Note that the shape may be classified in further detail. For example, the protruding type may be classified into one of a sessile type (Is) which does not have constriction at a rising portion, a semi-pedunculated type (Isp) which has constriction at the rising portion, and a pedunculated type (Ip) which has pedicle, and the surface type may be classified into one of an elevated type (IIa), a flat type (IIb) and a depressed type (IIc).

An oversight risk (a high oversight risk or a low oversight risk) is registered in each classification. For example, a low oversight risk is registered for the protruding type (type I), and a high oversight risk is registered for the surface type (type II). The lesion shape analysis unit 34A4 determines the oversight risk registered for the classification of the shape of the lesion area Ln as the oversight risk of the lesion area Ln. In other words, in a case where the shape of the lesion area Ln is classified into a shape (for example, the surface type (type II)) for which the high oversight risk is registered, the lesion shape analysis unit 34A4 determines that the oversight risk of the lesion area Ln is high. On the other hand, in a case where the shape of the lesion area Ln is classified into a shape (for example, the protruding type (type I)) for which the low oversight risk is registered, the lesion shape analysis unit 34A4 determines that the oversight risk of the lesion area Ln is low.

In a case where the oversight risk is judged in accordance with the state of the image, the image state analysis unit 34B of the oversight risk analysis unit 34 performs analysis processing for judging the risk. Analysis items for the oversight risk in accordance with the state of the image include, for example, (e) an exposure state, (f) a focus state, (g) a surface state of the object and (h) a lens state. The image state analysis unit 34B performs analysis concerning items selected from these items and judges a risk that the lesion area Ln may be overlooked.

(e) Exposure State

In a case where the present item is selected as the analysis item, an exposure state analysis unit 34B1 in FIG. 4 analyzes an exposure state of the observation image G1. In a case where exposure is not appropriate such as a case where the image is dark due to too short exposure time period of the image pickup device of the endoscope 2 and a case where halation which is white blur at a portion irradiated with intense light occurs, the exposure state analysis unit 34B1 determines that the oversight risk of the lesion area Ln is high. On the other hand, in a case where exposure is appropriate, the exposure state analysis unit 34B1 determines that the oversight risk of the lesion area Ln is low.

(f) Focus State

In a case where the present item is selected as the analysis item, a focus state analysis unit 34B2 in FIG. 4 analyzes the focus state of the observation image G1. In a case where focus control of a lens which constitutes an image pickup system of the endoscope 2 is not appropriately performed and the object is not focused on (in a case of so-called a state of out of focus), the focus state analysis unit 34B2 determines that the oversight risk of the lesion area Ln is high. On the other hand, in a case where the object is focused on, the focus state analysis unit 34B2 determines that the oversight risk of the lesion area Ln is low.

(g) Surface State of Object

In a case where the present item is selected as the analysis item, an object surface analysis unit 34B3 in FIG. 4 analyzes the state of the object in the observation image G1. In a case where the object has a residue, bleeding, a scar from treatment, or the like, it is determined that the oversight risk of the lesion area Ln is high. On the other hand, in a case where the object does not have a residue, bleeding, a scar from treatment, or the like, it is determined that the oversight risk of the lesion area Ln is low.

(h) State of Lens

In a case where the present item is selected as the analysis item, a lens state analysis unit 34B4 in FIG. 4 analyzes from the observation image G1 a state of a lens which constitutes an image pickup system of the endoscope 2. In a case where the lens is opaque or dirty, it is determined that the oversight risk of the lesion area Ln is high. On the other hand, in a case where the lens is neither opaque nor dirty, it is determined that the oversight risk of the lesion area Ln is low.

In a case where the oversight risk is judged in accordance with the operation state of the endoscope (the movement state of the lesion area in the image), a movement analysis unit 34C of the oversight risk analysis unit 34 performs analysis processing for judging the risk. The analysis items for the oversight risk in accordance with the operation state of the endoscope include, for example, (i) movement speed of the endoscope, and (j) change in the position of the lesion area Ln. The movement analysis unit 34C performs analysis concerning the items selected from these items and judges a risk that the lesion area Ln may be overlooked.

(i) Movement Speed of Lesion Area Ln

In a case where the present item is selected as the analysis item, a speed analysis unit 34C1 in FIG. 4 analyzes change of movement speed (pulling-out speed) of the endoscope. The speed analysis unit 34C1 compares movement speed of the endoscope 2 in a state before the lesion area Ln is detected with movement speed of the endoscope 2 in a state where the lesion area Ln is detected.

Normally, when the surgeon finds the lesion area Ln in the observation image G1, the surgeon lowers pulling-out speed (or stops pulling out) of the endoscope 2 to observe the lesion area Ln. In a case where the pulling-out speed of the endoscope 2 does not change although the lesion area Ln appears in the observation image G1, it is inferred that the surgeon is likely to overlook the lesion area Ln. Thus, in a case where change of the speed is smaller than a threshold set in advance, that is, in a case where change of the pulling-out speed of the endoscope 2 is small, it is determined that the oversight risk of the lesion area Ln is high.

On the other hand, in a case where change of the speed is greater than the threshold set in advance, that is, in a case where change of the pulling-out speed of the endoscope 2 is great, it is determined that the oversight risk of the lesion area Ln is low.

(j) Change of Position of Lesion Area Ln

In a case where the present item is selected as the analysis item, a position analysis unit 34C2 in FIG. 4 analyzes change of the position of the lesion area Ln in the observation image G1. The position analysis unit 34C2 continuously monitors the position of the lesion area Ln from a state where the lesion area Ln is detected in the observation image G1. In a case where the lesion area Ln moves outside the observation image G1 and becomes undetectable in the observation image G1, it is determined that the oversight risk of the lesion area Ln is high. On the other hand, while the lesion area Ln is continuously detected in the observation image G1, it is determined that the oversight risk of the lesion area Ln is low.

After the oversight risk analysis processing (S3) in the flowchart in FIG. 5 is finished as described above, a determination result of the oversight risk is output from the oversight risk analysis unit 34 to the notification control unit 35. The notification control unit 35 determines a notification method in accordance with the level of the input oversight risk (S4).

The notification control unit 35 controls a notification method of the support information in accordance with the risk that the lesion area may be overlooked, input from the oversight risk analysis unit 34. In a case where a notification of the oversight risk is made by displaying the support information (for example, a marker image) in a display image of the monitor 5, the notification control unit 35 changes color, a thickness or a size of the marker image to be added to the lesion area in accordance with the level of the oversight risk. For example, the notification control unit 35 makes the thickness of the marker image thicker in a case where the oversight risk is high and makes the thickness of the marker image thinner in a case where the oversight risk is low. Alternatively, for example, the notification control unit 35 makes the size of the marker image larger in a case where the oversight risk is high and makes the size of the marker image smaller in a case where the oversight risk is low.

Note that the number of items of the marker image to be changed is not limited to one, but a plurality of items may be changed in accordance with the level of the risk. For example, both the thickness and the size of the marker image may be changed. Further, it is also possible to make a change such that in a case where the oversight risk is low, only the marker image is displayed, and in a case where the oversight risk is high, types of the support information may be increased, for example, a pop-up message may be displayed in addition to the marker image.

Finally, the notification control unit 35 generates support information and makes a notification on the basis of the notification method determined in step S4 (S5). More specifically, the notification control unit 35 generates a marker image G2 in accordance with the level of the oversight risk as the support information and outputs the marker image G2 to the image superimposing unit 36. The image superimposing unit 36 outputs an endoscope image in which the marker image G2 input from the notification control unit 35 is superimposed on the observation image G1 input from the image input unit 31, to the monitor 5 and causes the endoscope image to be displayed.

Figure 6:
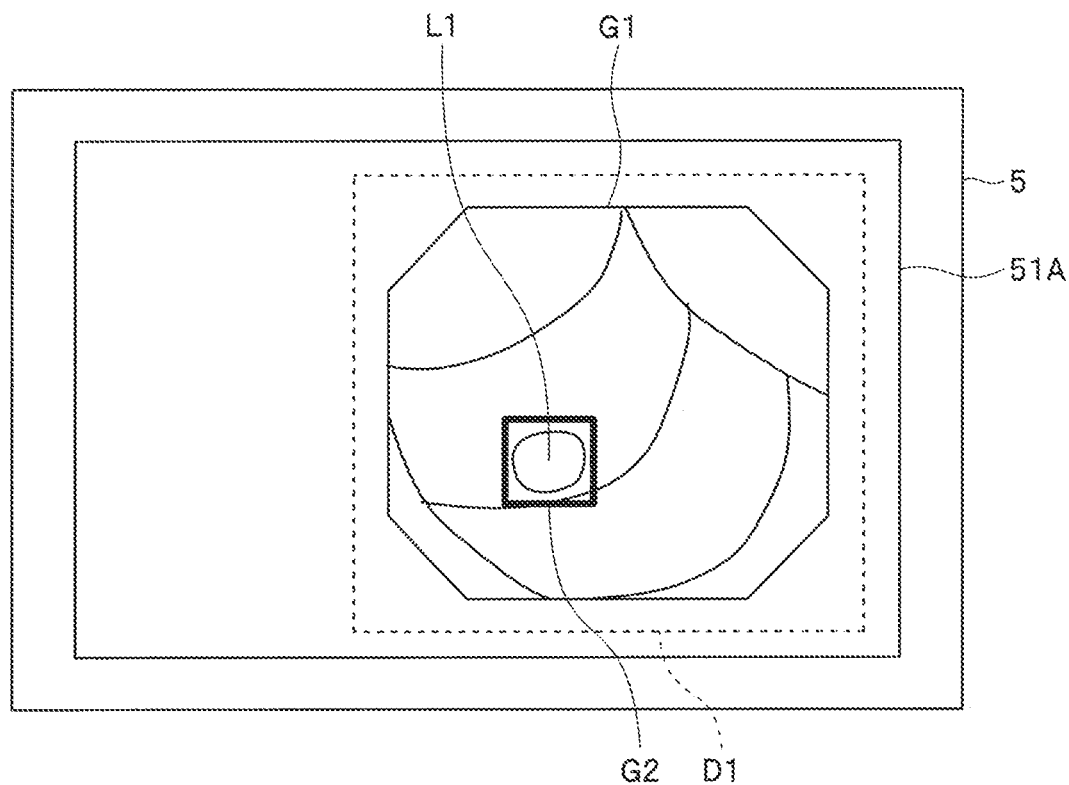
FIG. 6 is a view illustrating an example of an endoscope image to be displayed at a monitor 5.
Figure 7:
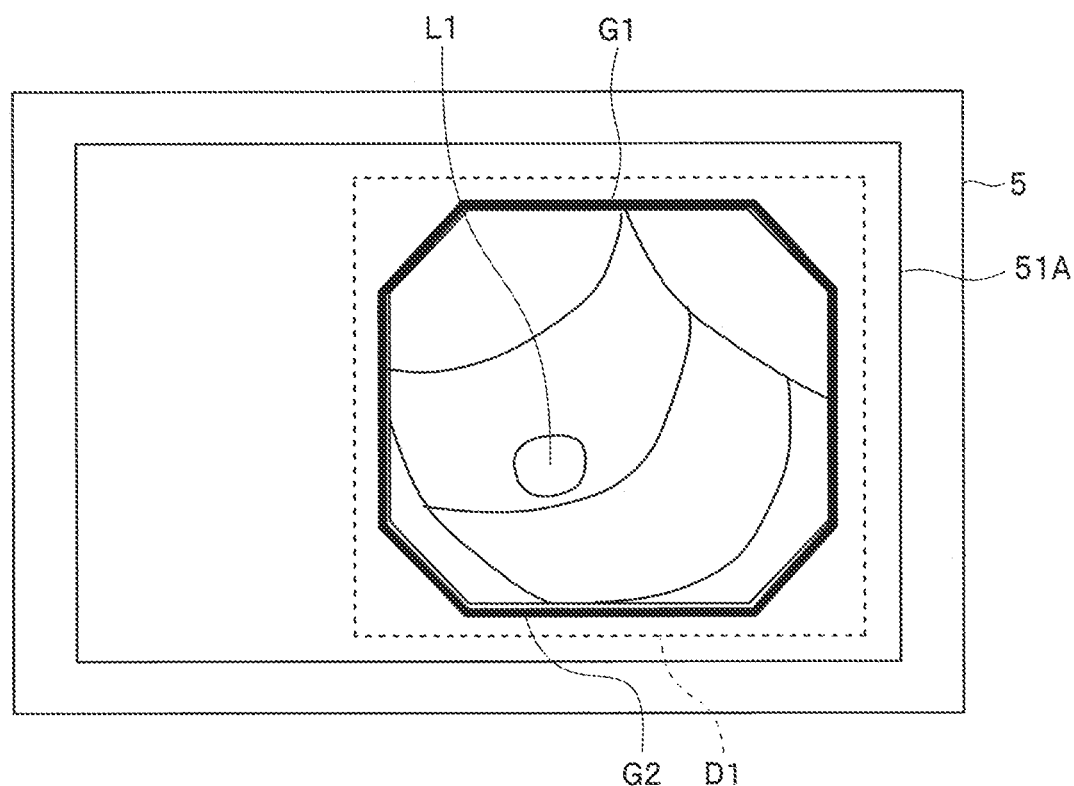
FIG. 7 is a view illustrating an example of an endoscope image to be displayed on the monitor 5.

FIG. 6 and FIG. 7 are views illustrating an example of the endoscope image displayed on the monitor 5. In other words, FIG. 6 and FIG. 7 illustrate endoscope images in which the support information is superimposed, FIG. 6 illustrates an example where the oversight risk is low, and FIG. 7 illustrates an example where the oversight risk is high.

As illustrated in FIG. 6 and FIG. 7, the observation image G1 to which the marker image G2 is added is displayed in a display region D1 on a display screen 51A of the monitor 5. As illustrated in FIG. 6, in a case where the oversight risk is low, the marker image G2 having a size enclosing the circumference of a lesion area L1 is superimposed on the observation image G1. On the other hand, as illustrated in FIG. 7, in a case where the oversight risk is high, the marker image G2 having a size enclosing a periphery portion of the observation image G1 is superimposed on the observation image G1. Further, a thickness of the marker image G2 illustrated in FIG. 7 is made thicker than a thickness of the marker image G2 illustrated in FIG. 6.

In this manner, according to the above-described embodiment, the oversight risk of the lesion area L1 is analyzed by analyzing the observation image G1, and the notification method of the support information for allowing the surgeon to recognize existence of the lesion area L1 is controlled in accordance with a level of the oversight risk. It is therefore possible to achieve an oversight prevention function at low cost without impairing user-friendliness.

Note that while the level of the oversight risk is classified into two levels of high and low in the above description, the level of the oversight risk may be classified into three or more levels, and the notification method of the support information may be controlled in accordance with the respective levels.

Further, while the image generation unit within the processor 4, which is not illustrated, generates the observation image on the basis of the image pickup signal obtained by picking up an image of the object at the endoscope 2 in the above description, it is also possible to employ a configuration where an image processing apparatus, which is provided between the endoscope 2 and the processor 4, generates the observation image, and the processor 4 generates the support information using the input observation image.

Second Embodiment

In the above-described first embodiment, when an image of the support information is displayed on the monitor 5, a display method is changed in accordance with the level of the oversight risk, and a notification is made. In contrast, the present embodiment is different from the first embodiment in that notification means other than notification using display of an image is used, and a notification is made using a plurality of types of notification means.

An endoscope system of the present embodiment has a configuration similar to the configuration of the endoscope system 1 in the first embodiment. The endoscope system of the present embodiment has features in a configuration of the notification control unit 35 of the computation unit 22b. A detailed configuration of the notification control unit 35 will be described below using FIG. 8. Note that the same reference numerals will be assigned to the same components, and description will be omitted.

Figure 8:
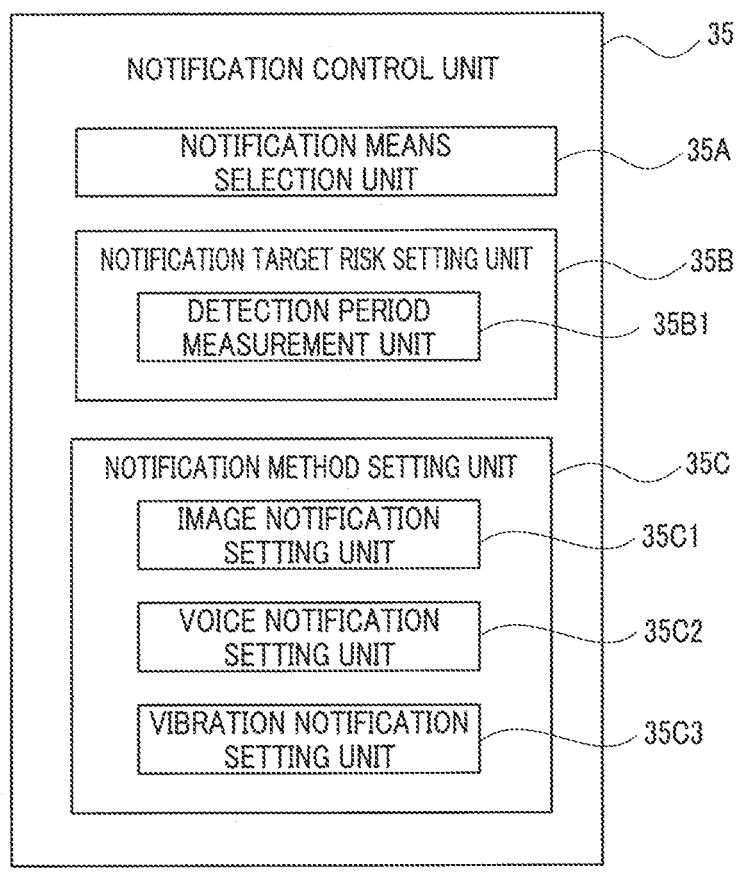
FIG. 8 is a block diagram illustrating a configuration of a notification control unit 35 according to a second embodiment.

FIG. 8 is a block diagram illustrating a configuration of the notification control unit 35 according to the second embodiment. The notification control unit 35 includes a notification means selection unit 35A, a notification target risk setting unit 35B, and a notification method setting unit 35C.

The notification means selection unit 35A selects means for making a notification that the support information is displayed on the monitor 5. The notification means which can be selected includes a notification using voice from a speaker 5a (hereinafter, referred to as a voice notification), a notification using vibration of a portion such as the operation portion 10 grasped by the surgeon (hereinafter, referred to as a vibration notification), or the like, in addition to the above-described display of an image on the monitor 5 (hereinafter, referred to as an image notification).

The notification target risk setting unit 35B sets an oversight risk for which a notification is to be controlled. The oversight risk which can be set is a risk for which the level of the risk can be determined on the basis of the analysis result of the oversight risk analysis unit 34. Setting items include, for example, (A) the number of detected lesion areas Ln, (B) a degree of difficulty in finding the lesion area Ln, (C) a size of the lesion area Ln, (D) a type of the lesion area Ln, (E) detection reliability of the lesion area Ln, and (F) an elapsed time period since the lesion area Ln has been detected. The notification target risk setting unit 35B selects an item to be set as the notification target risk among these setting items.

(A) The Number of Detected Lesion Areas Ln

The present item is an oversight risk determined on the basis of the number of lesion areas Ln existing in the observation image G1. The number of lesion areas Ln existing in the observation image G1 is detected at a lesion number analysis unit 34A5 of the oversight risk analysis unit 34. The lesion number analysis unit 34A5 determines the oversight risk on the basis of the number of lesion areas Ln detected in the observation image G1. In other words, in a case where the number of lesion areas Ln is larger than a threshold (for example, two) set in advance, it is determined that the oversight risk is low. On the other hand, in a case where the number of lesion areas Ln is equal to or less than the threshold set in advance, it is determined that the oversight risk is high.

(B) Degree of Difficulty in Finding Lesion Area Ln

The present item is an oversight risk determined while oversight risks based on the shape, the position, the size, and the like, of the lesion area Ln are comprehensively taken into account. More specifically, the degree of difficulty in finding the lesion area Ln is judged using analysis results or risk determination results at the lesion shape analysis unit 34A4, the lesion position analysis unit 34A2 and the lesion size analysis unit 34A1 of the oversight risk analysis unit 34. For example, in a case where the lesion area Ln has a protruding shape, the lesion area Ln is located near the center of the observation image G1 or the size of the lesion area Ln is large, it is judged that the degree of difficulty in finding the lesion area Ln is small. Further, for example, in a case where the lesion area Ln has a flat shape, the lesion area Ln is located near the periphery portion of the observation image G1 or the size of the lesion area Ln is small, it is judged that the degree of difficulty in finding the lesion area Ln is large. In a case where the degree of difficulty in finding the lesion area Ln is small, it is determined that the oversight risk is low. On the other hand, in a case where the degree of difficulty in finding the lesion area Ln is large, it is determined that the oversight risk is high.

(C) Size of Lesion Area Ln

The present item is an oversight risk determined on the basis of the size of the lesion area Ln. The oversight risk determined at the lesion size analysis unit 34A1 of the oversight risk analysis unit 34 is used.

(D) Type of Lesion Area Ln

The present item is an oversight risk determined in accordance with the type of the lesion area Ln based on the shape and a degree of seriousness. More specifically, the oversight risk is determined using the analysis results or the risk determination results of the lesion shape analysis unit 34A4 of the oversight risk analysis unit 34 and a lesion seriousness analysis unit 34A6.

The lesion seriousness analysis unit 34A6 analyzes the degree of seriousness of the lesion area Ln on the basis of whether a tumor which is the lesion area Ln is benign or malignant. Whether the tumor is benign or malignant is determined, for example, by observing a state of a boundary between the tumor and a normal mucous portion, and it is determined that the tumor is malignant in a case where the boundary is unclear and has a non-uniform shape such as a jagged shape, and determined that the tumor is benign in a case where the boundary is clear. In a case where the tumor is benign, it is determined that the degree of seriousness is low, and the oversight risk is low, and in a case where the tumor is malignant, it is determined that the degree of seriousness is high, and the oversight risk is high.

In a case where the lesion area Ln has a protruding shape and the degree of seriousness is low, it is determined that the oversight risk is low. On the other hand, in a case where the lesion area Ln has a flat shape and the degree of seriousness is high, it is determined that the oversight risk is high.

(E) Detection Reliability of Lesion Area Ln

The present item is an oversight risk determined while the oversight risks based on the states of the image (the exposure state, the focus state, the surface state of the object and the state of the lens) are comprehensively taken into account. More specifically, the detection reliability is judged using the analysis result or the risk determination result at the image state analysis unit 34B of the oversight risk analysis unit 34.

For example, in a case where the exposure state is appropriate, the object is focused on, there is no residue, bleeding or scar from treatment on the surface of the object, or the lens is neither opaque nor dirty, it is judged that the detection reliability is high. On the other hand, in a case where the exposure state is not appropriate, the object is not focused on, there is a residue, bleeding or a scar from treatment on the surface of the object, or the lens is opaque or dirty, it is judged that the detection reliability is low. In a case where the detection reliability is high, it is determined that the oversight risk is low. On the other hand, in a case where the detection reliability is low, it is determined that the oversight risk is high.

(F) Elapsed Time Period Since Lesion Area Ln has been Detected

The present item is an oversight risk determined on the basis of an elapsed time period since the lesion area Ln has been detected, which is a time period during which the lesion area Ln is continuously detected since the lesion area Ln has been detected in the observation image G1. The elapsed time period since the lesion area Ln has been detected is measured at a detection period measurement unit 35B1. In a case where the elapsed time period since the lesion area Ln has been detected is shorter than a threshold (for example, five seconds) set in advance, it is determined that the oversight risk is low. On the other hand, in a case where the elapsed time period since the lesion area Ln has been detected is equal to or greater than the threshold set in advance, it is determined that the oversight risk is high.

The notification methods using respective kinds of notification means are set at the notification method setting unit 35C. The notification method setting unit 35C extracts a notification method corresponding to the oversight risk for which a notification is to be controlled, set at the notification target risk setting unit 35B, from notification methods set in advance for the respective kinds of notification means selected at the notification means selection unit 35A. Then, the selected notification means is controlled in accordance with the extracted notification method.

A notification method using an image notification is set in an image notification setting unit 35C1. Further, a notification method using a voice notification and a notification method using a vibration notification are respectively set in a voice notification setting unit 35C2 and in a vibration notification setting unit 35C3. An example of setting content at each notification setting unit will be described below.

First, an example of setting content of the image notification setting unit 35C1 will be described. The setting content will be described for each item set as the notification target risk.

(A) The Number of Detected Lesion Areas Ln

A notification is made regardless of a level of the oversight risk. However, color and a size of the marker G2 are made different in accordance with the oversight risk. For example, in a case where the oversight risk is low, green is set as the color of the marker image G2, and in a case where the oversight risk is high, red is set as the color of the marker image G2. The marker image G2 may be blinked the number of times corresponding to the number of detected lesion areas Ln, or flags of the number corresponding to the number of detected lesion areas Ln may be displayed at the marker image G2.

(B) Degree of Difficulty in Finding Lesion Area Ln

A notification is made regardless of a level of the oversight risk.

(C) Size of Lesion Area Ln

A notification is made regardless of a level of the oversight risk.

(D) Type of Lesion Area Ln

A notification is made regardless of a level of the oversight risk.

(E) Detection Reliability of Lesion Area Ln

A notification is made regardless of a level of the oversight risk.

(F) Elapsed Time Period Since Lesion Area Ln has been Detected

A display start timing and a display period of the marker image G2 are made different in accordance with the oversight risk. For example, the marker image G2 is not displayed in a stage at which the elapsed time period since the lesion area Ln has been detected is shorter than a threshold and the oversight risk is low, and display of the marker image is started at a timing at which the elapsed time period since the lesion area Ln has been detected exceeds the threshold and the oversight risk becomes high. Further, for example, in a case where the elapsed time period since the lesion area Ln has been detected is long, the display period of the marker image G2 is set longer.

An example of setting content of the voice notification setting unit 35C2 will be described next.

(A) The Number of Detected Lesion Areas Ln

A notification is made regardless of a level of the oversight risk. However, voice notification content is made different in accordance with the oversight risk. For example, an alert is issued the number of times corresponding to the number of detected lesion areas Ln. Alternatively, for example, settings may be made such that in a case where the oversight risk is low, the volume of the voice is lowered or tone may be lowered, and in a case where the oversight risk is high, the volume of the voice is increased or tone is made higher.

(B) Degree of Difficulty in Finding Lesion Area Ln

Settings are made such that in a case where the oversight risk is low, the volume of the voice is lowered or tone is lowered, and in a case where the oversight risk is high, the volume of the voice is increased or tone is made higher. Alternatively, settings may be made such that a voice notification is not made in a case where the oversight risk is low, and a voice notification is made only in a case where the oversight risk is high.

(C) Size of Lesion Area Ln

Settings are made such that in a case where the oversight risk is low, the volume of the voice is lowered or tone is lowered, and in a case where the oversight risk is high, the volume of the voice is increased or tone is made higher. Alternatively, settings may be made such that a voice notification is not made in a case where the oversight risk is low, and a voice notification is made only in a case where the oversight risk is high.

(D) Type of Lesion Area Ln

Settings are made such that in a case where the oversight risk is low, the volume of the voice is lowered or tone is made lower, and in a case where the oversight risk is high, the volume of the voice is increased or tone is made higher. Alternatively, in a case where an image notification and a voice notification are made in combination, settings may be made such that a voice notification is not made in a case where the oversight risk is low, and a voice notification is made only in a case where the oversight risk is high. In a case where a voice notification and a vibration notification are made in combination, settings may be made such that the notifications are made regardless of a level of the oversight risk.

(E) Detection Reliability of Lesion Area Ln

In a case where an image notification and a voice notification are made in combination, settings are made such that a voice notification is not made in a case where the oversight risk is low, and a voice notification is made only in a case where the oversight risk is high. Further, in a case where a voice notification and a vibration notification are made in combination, settings are made such that the notifications are made regardless of a level of the oversight risk.

(F) Elapsed Time Period Since Lesion Area Ln has been Detected

A notification is made from a detection start time point regardless of a level of the oversight risk. Note that an alert period may be set in accordance with the oversight risk or may be set at a predetermined set period. In a case where the alert period is set at the predetermined set period, an alert is stopped if a period exceeds the set period even if the lesion area Ln is continuously detected.

An example of setting content of a vibration notification setting unit 35C3 will be described last.

(A) The Number of Detected Lesion Areas Ln

A notification is made regardless of a level of the oversight risk. However, vibration notification content is made different in accordance with the oversight risk. For example, the notification means is caused to vibrate the number of times corresponding to the number of detected lesion areas Ln. Alternatively, for example, settings may be made such that a vibration frequency is made lower in a case where the oversight risk is low, and the vibration frequency is made higher in a case where the oversight risk is high. Note that a vibration pattern may be made different in accordance with the oversight risk.

(B) Degree of Difficulty in Finding Lesion Area Ln

Settings are made such that the vibration frequency is made lower in a case where the oversight risk is low, and the vibration frequency is made higher in a case where the oversight risk is high. The vibration pattern may be changed in accordance with the oversight risk. Note that in a case where both an image notification and a vibration notification are made, settings may be made such that a vibration notification is not performed in a case where the oversight risk is low, and a vibration notification is made only in a case where the oversight risk is high. Further, in a case where both a voice notification and a vibration notification are made, settings are made such that the notifications are made regardless of a level of the oversight risk.

(C) Size of Lesion Area Ln

Settings are made such that the vibration frequency is made lower in a case where the oversight risk is low, and the vibration frequency is made higher in a case where the oversight risk is high. The vibration pattern may be changed in accordance with the oversight risk. Note that in a case where an image notification and a vibration notification are made in combination, settings may be made such that a vibration notification is not performed in a case where the oversight risk is low, and a vibration notification is made only in a case where the oversight risk is high. Further, in a case where a voice notification and a vibration notification are made in combination, settings may be made such that the notifications are made regardless of a level of the oversight risk.

(D) Type of Lesion Area Ln

Settings are made such that the volume of the voice is lowered or tone is made lower in a case where the oversight risk is low, and the volume of the voice is increased or tone is made higher in a case where the oversight risk is high. Alternatively, in a case where an image notification and a voice notification are made, settings may be made such that a voice notification is not made in a case where the oversight risk is low, and a voice notification is made only in a case where the oversight risk is high. In a case where a voice notification and a vibration notification are made in combination, settings may be made such that the notifications are made regardless of a level of the oversight risk.

(E) Detection Reliability of Lesion Area Ln

Settings are made such that a vibration notification is not made in a case where the oversight risk is low, and a vibration notification is made only in a case where the oversight risk is high.

(F) Elapsed Time Period Since Lesion Area Ln has been Detected

In a case where an image notification and a vibration notification are made in combination, the notifications are made from a detection start time point regardless of a level of the oversight risk. On the other hand, in a case where a voice notification and a vibration notification are made in combination, a vibration notification is not made while the oversight risk is low, and the notification is made from a time point at which the oversight risk becomes high. Note that an alert period may be set in accordance with the oversight risk or may be set at a predetermined set period. In a case where the alert period is set at the predetermined set period, an alert is stopped if a period exceeds the set period even if the lesion area Ln is continuously detected in a case where an image notification and a vibration notification are made in combination. In a case where a voice notification and a vibration notification are made in combination, the notifications are continuously made while the lesion area Ln is continuously detected.

Procedure of executing a diagnosis support function to be performed using the endoscope system configured as described above is similar to the diagnosis support procedure in the first embodiment illustrated in FIG. 5. However, in determination of notification methods in S4, notification methods in accordance with the set oversight risk are set for a plurality of kinds of notification means selected by the surgeon.

For example, in a case where an image notification and a voice notification are selected, and (A) the number of detected lesion areas Ln is set as the notification target risk, the notification method setting unit 35C sets an image notification method at the image notification setting unit 35C1 and sets a voice notification method at the voice notification setting unit 35C2. For example, the image notification setting unit 35C1 makes settings so as to blink the marker image G2 the number of times corresponding to the number of detected lesion areas Ln, and the voice notification setting unit 35C2 makes settings so as to issue an alarm the number of times corresponding to the number of detected lesion areas.

In this manner, according to the above-described embodiments, a notification of the support information is made using a plurality of kinds of notification means, and notification methods of the support information for allowing the surgeon to recognize existence of the lesion area L1 are controlled in accordance with combination of the level of the oversight risk and the selected notification means. It is therefore possible to achieve an oversight prevention function at low cost without impairing user-friendliness.

Note that the notification means is not limited to the above-described three types (image, voice, vibration), but other means may be combined. Further, notification target risk items, and specific notification methods are not limited to the above-described example. Still further, while a case has been described in the above-described example where two types of notification means are combined, three or more types of notification means may be combined.

Third Embodiment

In the above-described first embodiment, only one image display region D1 is disposed on the display screen 51A of the monitor 5. In contrast, the present embodiment is different from the first embodiment in that two image display regions D1 and D2 are disposed on the display screen 51A, and notification methods in the respective display regions D1 and D2 are controlled in accordance with a level of the oversight risk.

An endoscope system of the present embodiment has a configuration similar to the configuration of the endoscope system 1 in the first embodiment. The endoscope system of the present embodiment has features that the notification control unit 35 generates support information in accordance with the oversight risk of the lesion area Ln respectively for the two display regions D1 and D2 and causes the support information to be displayed on the monitor 5. Description will be provided below using FIG. 9.

Figure 9:
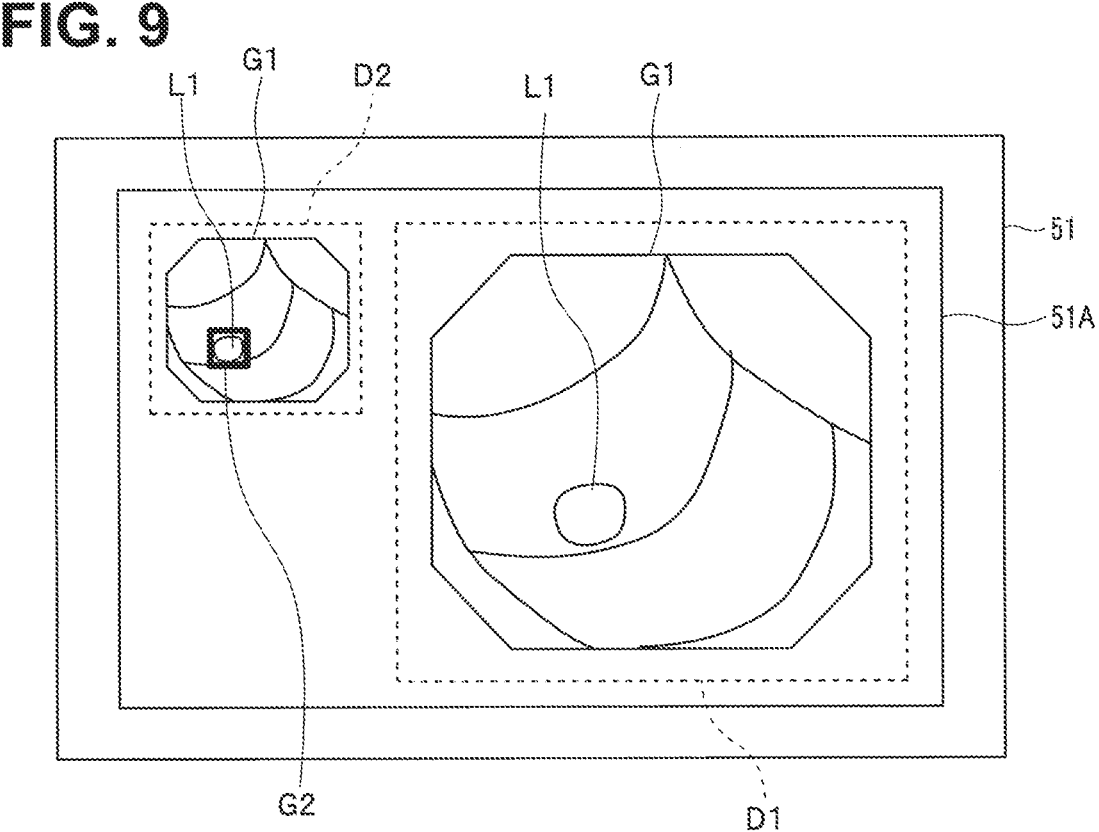
FIG. 9 is a view illustrating an example of an endoscope image generated by an image superimposing unit 36 according to a third embodiment.

FIG. 9 is a view illustrating an example of an endoscope image generated by the image superimposing unit 36 according to the third embodiment. As illustrated in FIG. 9, two display regions of the display region D1 in which the observation image G1 is displayed, and the display region D2 having a size smaller than a size of the display region D1 are disposed on the display screen 51A of the monitor 5. Normally, the surgeon performs procedure while observing the endoscope image displayed in the display region D1 as a main screen, and an image (for example, an enlarged image of a specific region) which supports observation of the endoscope image displayed in the display region D1, a recorded image, or the like, is displayed in the display region D2 as a sub-screen.

In the present embodiment, a notification method of the support information (marker image G2) to be displayed in the display region D1 is made different from a notification method of the marker image G2 to be displayed in the display region D2. In other words, the marker image G2 to be displayed in the display region D2 increases sensitivity for the oversight risk. For example, the marker image G2 is displayed only in the display region D2 in a case where the oversight risk of the lesion area Ln is low, and the marker image G2 is displayed in both the display regions D1 and D2 in a case where the oversight risk of the lesion area Ln is high.

In this manner, according to the present embodiment, it is possible to prevent the marker image G2 from inhibiting procedure by displaying the marker image G2 which is support information with lowered risk sensitivity, in a region in which an endoscope image which is mainly observed by the surgeon is displayed. Further, it is possible to prevent the lesion area Ln from being overlooked by displaying the marker image G2 which is support information with increased risk sensitivity, in the sub-screen. It is therefore possible to achieve an oversight prevention function at low cost without impairing user-friendliness.

Note that the notification methods of the support information in accordance with the oversight risk may be controlled by a format of the marker image G2 (such as a thickness, color, a size and whether or not blinked) as well as being controlled by the display timing of the marker image G2. Further, the level of the oversight risk is not limited to two stages, and the notification methods of the support information may be controlled in accordance with the level which includes three or more stages.

The present invention is not limited to the above-described embodiments, of course, various modifications and application are possible within the range not deviating from the gist of the present invention.

What is claimed is:

1. An endoscope system comprising:
a processor including hardware; and
a display apparatus,
the processor being configured to:
sequentially input a plurality of observation images obtained by picking up images of an object with an endoscope,
detect from the observation images a lesion area which is an observation target of the endoscope,
judge a level of an oversight risk which is a risk that an operator overlooks the lesion area, on a basis of the observation images, and
control notification methods of detection of the lesion area on a basis of the level of the oversight risk,
the display apparatus including a first image region and a second image region that are for displaying a marker image indicating the lesion area, the second image region being smaller than the first image region, to notify the operator of detection of the lesion area on a basis of control of the notification methods,
the processor causing the marker image to be displayed only in the second image region in a case where a level of the oversight risk relating to the lesion area is a first level and causing the marker image to be displayed in both the first image region and the second image region in a case where a level of the oversight risk relating to the lesion area is a second level higher than the first level.

2. The endoscope system according to claim 1, wherein the processor analyzes the oversight risk on a basis of a state of the lesion area.

3. The endoscope system according to claim 2, wherein the processor estimates a size of the lesion area.

4. The endoscope system according to claim 2, wherein the processor analyzes a position of the lesion area in the observation images.

5. The endoscope system according to claim 2, wherein the processor includes a lesion density analysis unit configured to analyze density of the lesion area.

6. The endoscope system according to claim 2, wherein the processor analyzes a shape of the lesion area.

7. The endoscope system according to claim 1,
wherein the processor analyzes the oversight risk on a basis of a state of the observation images.

8. The endoscope system according to claim 7,
wherein the processor analyzes an exposure state of the observation images.

9. The endoscope system according to claim 7,
wherein the processor analyzes a degree of focusing of a focus of the observation images.

10. The endoscope system according to claim 7,
wherein the processor analyzes whether or not a residue or bleeding exists in the observation images.

11. The endoscope system according to claim 7,
wherein the processor analyzes whether or not the observation images are opaque or dirty.

12. The endoscope system according to claim 1,
wherein the processor analyzes the oversight risk on a basis of a movement state of the lesion area in the observation images.

13. The endoscope system according to claim 12,
wherein the processor analyzes change of movement speed of the lesion area in the observation images.

14. The endoscope system according to claim 12,
wherein the processor analyzes change of a position of the lesion area in the observation images.

15. The endoscope system according to claim 1,
wherein the processor performs notification control to generate a marker image indicating the lesion area and superimpose the marker image on the observation images and makes at least one of color, a thickness or a size of the marker image different in accordance with a level of the oversight risk of the lesion area.

16. The endoscope system according to claim 1,
wherein the display apparatus is provided in plurality, and each of the display apparatuses makes notification of detection of the lesion area using notification means different from each other.

17. The endoscope system according to claim 16,
wherein the processor selects a display apparatus which becomes a notification target from the display apparatus in plurality and controls the notification methods for the selected display apparatus.

18. The endoscope system according to claim 16,
wherein the notification means is one of an image, voice or vibration.

19. The endoscope system according to claim 17,
wherein the notification method setting unit determines the notification methods for the respective notification means in accordance with a combination of the notification means in plurality selected by a notification means selection unit.

20. An endoscope image processing method comprising:
sequentially inputting a plurality of observation images obtained by picking up images of an object with an endoscope;
detecting from the observation images a lesion area which is an observation target of the endoscope;
judging a level of an oversight risk which is a risk that an operator overlooks the lesion area, on a basis of the observation images;
controlling notification methods of detection of the lesion area on a basis of the level of the oversight risk;
notifying the operator of detection of the lesion area on a basis of control of the notification methods using a display apparatus including a first image region and a second image region that are for displaying a marker image indicating the lesion area, the second image region being smaller than the first image region; and
causing the marker image to be displayed only in the second image region in a case where a level of the oversight risk relating to the lesion area is a first level and causing the marker image to be displayed in both the first image region and the second image region in a case where a level of the oversight risk relating to the lesion area is a second level higher than the first level.

21. A computer-readable storage medium which is a non-transitory computer-readable recording medium storing a program executed by a computer, the computer-readable storage medium storing an endoscope image processing program for causing the computer to execute:
sequentially acquiring a plurality of observation images obtained by picking up images of an object with an endoscope;
detecting from the observation images a lesion area which is an observation target of the endoscope;
judging a level of an oversight risk which is a risk that an operator overlooks the lesion area, on a basis of the observation images;
controlling notification methods of detection of the lesion area on a basis of the level of the oversight risk;
notifying the operator of detection of the lesion area on a basis of control of the notification methods using a display apparatus including a first image region and a second image region that are for displaying a marker image indicating the lesion area, the second image region being smaller than the first image region; and
displaying the marker image only in the second image region in a case where a level of the oversight risk relating to the lesion area is a first level and displaying the marker image in both the first image region and the second image region in a case where a level of the oversight risk relating to the lesion area is a second level higher than the first level.

* * * * *